US005859261A

United States Patent [19]
Faul et al.

[11] Patent Number: 5,859,261
[45] Date of Patent: *Jan. 12, 1999

[54] SYNTHESIS OF INDOLYLMALEIMIDES

[75] Inventors: Margaret M. Faul, Zionsville; Michael R. Jirousek, Indianapolis; John H. McDonald, III, Carmel; David Andrew Neel, Zionsville, all of Ind.

[73] Assignee: Eli Lilly and Company, Indianapolis, Ind.

[*] Notice: This patent issued on a continued prosecution application filed under 37 CFR 1.53(d), and is subject to the twenty year patent term provisions of 35 U.S.C. 154(a)(2).

[21] Appl. No.: 994,445

[22] Filed: Dec. 19, 1997

Related U.S. Application Data

[62] Division of Ser. No. 821,356, Mar. 20, 1997.
[51] Int. Cl.$^6$ .................................................. C07D 403/02
[52] U.S. Cl. ............................................................ 548/466
[58] Field of Search ............................................. 548/466

[56] References Cited

U.S. PATENT DOCUMENTS

| | | | |
|---|---|---|---|
| 4,785,085 | 11/1988 | Kaneko et al. | 536/27.1 |
| 5,057,614 | 10/1991 | Davis et al. | 548/466 |
| 5,292,747 | 3/1994 | Davis et al. | 514/285 |
| 5,380,746 | 1/1995 | Barth et al. | 514/414 |
| 5,399,712 | 3/1995 | Hill et al. | 548/466 X |
| 5,405,864 | 4/1995 | Broka et al. | 548/466 X |
| 5,545,636 | 8/1996 | Heath, Jr. et al. | 548/466 X |
| 5,668,152 | 9/1997 | Heath, Jr. et al. | 548/466 X |
| 5,672,618 | 9/1997 | Heath, Jr. et al. | 548/466 X |

FOREIGN PATENT DOCUMENTS

| | | |
|---|---|---|
| 0 540 956 | 5/1993 | European Pat. Off. . |
| 0 624 586 | 5/1994 | European Pat. Off. . |
| 0 657 411 | 6/1995 | European Pat. Off. . |
| 91/13071 | 9/1991 | WIPO . |

OTHER PUBLICATIONS

Greene et al., "Protective Groups in Organic Synthesis", 2nd Ed., 1991, John Wiley & Sons, Inc., New York, pp. 385–394 and 397–403.

R A Bit, et al., "Inhibitors of Protein Kinase C. E. Potent and Highly Selective Bisindoylmaleimides by Conformational Restriction", J. Med. Chem. 1993, 36, 21–29.

Peter A. Davis, et al., "Inhibitors of Protein Kinase C. 1,$^1$2.3–Bisarylmaleimides", J. Med. Chem. 1992, 35, 177–184.

C.S. Rooney, et al., "Inhibitors of Glycolic Acid Oxidase. 4–Substituted 3–Hydroxy–1H–pyrrole–2,5–dione Derivatives", J. Med. Chem. 1983, 26, 700–714.

Mercedes Amat, et al. "Preparation and Reactions of 10(tert–Butyldimethylsilyl)–3–lithiondol. Regioselective Synthesis of 3–Substituted Indoles", J. Org. Chem. 1994,59, 10–11.

Sharada S. Labadie, et al., "Indol–2–yltributylstannane: A versatile Reagent for 2–Substituted Indoles$^{1n}$", J. Org. Chem. 1994, 59, 4250–5254.

J.T. Link, et al., "First Total Synthesis of Staurosporine and ent–Staurosporine", J. Am. Chem. Soc. 1995, 117, 552–553.

Qu Zheng, "Vinylation of the Indole 3–Position Via Palladium–Catalyzed Cross–Coupling", Heterocycles, vol. 37, No. 3, 1994, pp. 1761–1772.

Samuel C. Conway, et al., "Synthesis of 1–(Phenylsulfonyl)Indol–3–yl Trifluoromethanesulfonate", Heterocycles, vol. 30, No. 1, 1990, pp. 627–633.

Harold F. Hodson, et al., "Regioselective Electrophilic Fluorination of Alkenyl and Related Stannanes Using Caesium Floroxysulfonate", Synlett, Oct. 1992, pp. 831–832.

Pier Giuseppe Ciattini, et al., "An Efficient Synthesis of 3–Substituted Indoles by Palladium–Catalyzed Coupling Reactions of 3–Tributylstannylindoles with Organic Triflates and Halides", Tetrahedron Letters, vol. 35, No. 15, pp. 2405–2408, 1994.

"Palladium Catalyzed Cross–Coupling Reaction between 3–Indole Boronic Acids and Tetrahydropyridine Triflates", Tetrahedron Letters, vol.34, No. 14, pp. 2235–2238, 1993.

Mercedes Amat, et al., "Palladium–Catalyzed Heterozrylation of 1–(tert–Butyldimethylsily)–3–indolylzinc Chloride. Efficient Synthesis of 3–(2–Pyridyl)indoles", Tetrahedron Letters, vol.35, No. 5, pp. 793–796, 1994.

William Harris, et al., "Oxidative Cyclisations with Palladium Aceta. A short Synthesis of Staurosporine Agylcone.", Tetrahedron Letters, vol.34, No. 51, pp. 8361–8364, 1993.

Guojian Xie, et al., "A Facile Synthsis of Staurosporine Aglycone", Tetrahedron Letters, vol.35, No. 31, pp. 5555–5558, 1994.

J. Bergman, et al., "Coupling of Indoleacetic Acid Trianion or Methyl Infoleacetic Acid Dianion. A Biomimetic Approach to Indolocarbazole Alxaloids.",Tetrahedron Letters, vol.28, No. 38, pp. 4441–4444, 1987.

Peter D. Davis, et al, "A Mild Conversion of Maleic Anhydrides Into Maleimides", Tetrahedron Letters, vol.31, No. 36, pp. 5201–5204, 1990.

Michael Brenner, et al., Synthesis of Arcyriarubin B and Related Bisindolymaleides$^{1n}$,Tetrahedron Letters, vol.44, No. 10, pp. 2887–2892, 1988.

Stephen Edge, et al., "An Improved Procedure for the Synthesis of N–substitued 3,4–dichloromaleimides", Chem. & Industry, Feb. 1991, p. 130.

*Primary Examiner*—Fiona T. Powers
*Attorney, Agent, or Firm*—Janelle D. Strode

[57] ABSTRACT

The present invention provides a method for synthesizing indolylmaleimides by reacting an activated maleimide preferably with an optionally substituted organometallic-3-indole in the presence of a transition metal catalyst.

11 Claims, No Drawings

SYNTHESIS OF INDOLYLMALEIMIDES

This application is a divisional of Ser. No. 08/821,356 filed Mar. 20, 1997, now pending.

BACKGROUND OF THE INVENTION

1. Field of the Invention

The present invention is broadly directed to an improved method for synthesizing indolylmaleimides, particularly bisindolylmaleimides, and especially non-symmetrical bisindolylmaleimides. In a more particular aspect, the present invention relates to an improved method of producing these indolylmaleimides using organometallic chemistry. In yet other aspects, the present invention is directed to a novel intermediate useful for preparing bisindolylmaleimides and to a novel intermediate step in the synthesis of bisindolylmaleimides.

2. Description of Related Art

Protein kinase C (PKC), and particularly its various isozymes, have been associated with a variety of disease states including cancer, central nervous system disorders, Alzheimer's, cardiovascular disease, dermatological diseases, inflammation, autoimmune diseases such as rheumatoid arthritis, and diabetic complications. As a result, there is a high level of research aimed at identifying therapeutic agents for inhibiting PKC activity as a way of treating these various conditions, and especially PKC inhibitors that are isozyme selective. Substituted indolylmaleimides, and particularly substituted bisindolylmaleimides, are one major class of compounds which have been found to be selective PKC inhibitors. (Steglich et al., *Angew. Chem. Int. Ed. Engl.* (1980), 19, 459). A wide variation of substituted bisindolylmaleimides are known in the art. Compounds based on such bisindolylmaleimides wherein the indolyl nitrogens are linked together through various moieties also have shown promise as selective PKC inhibitors. As a result, the prior art has describe a wide variety of such compounds and major investigations are directed to these materials.

A variety of approaches have been reported in the literature for synthesizing such indolylmaleimides (Bit et al., *J. Med. Chem.*, 36:21–29 (1993); Bit et al., *Tetrahedron Lett*, 34: 5623 (1993); Bergman et al., *Tetrahedron Lett.*, 28:4441–4444 (1987); Davis et al., *Tetrahedron Lett.*, 31:2353 (1990); Davis et al., *Tetrahedron Lett.*, 31:5201–5204 (1990); and Brenner et al., *Tetrahedron Lett.*, 44: 2887–2892 (1988)). Nevertheless, the art continues to look for additional approaches that permit higher yields, easier (e.g. milder) reaction conditions, less complicated process steps, a broader range of potential substituents and the like.

One of the more commonly used approaches for preparing bisindolylmaleimides, generally described by this literature, involves the condensation of an indole-1-Grignard reagent with a dihalomaleimide according to the following:

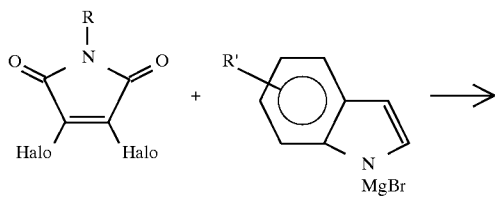

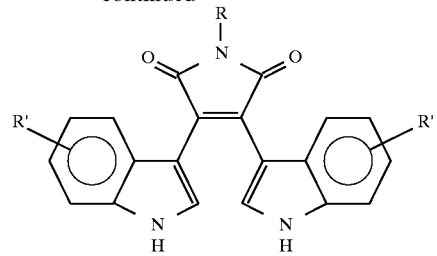

Generally, this reaction is carried out in an inert solvent such as benzene, toluene, tetrahydrofuran or ether at a temperature between room temperature and reflux temperature of the reaction mixture. The indole Grignard reagent is preferably prepared in situ from the indole and an alkyl magnesium halide such as ethyl magnesium bromide or ethyl magnesium iodide in a manner known in the art.

The reaction depicted above has been found to be dependent on solvent conditions. When carried out in a toluene:THF:ether solvent system this reaction provides the bisindolylmaleimide in greater than 80 percent yield and greater than 95 percent purity. Monosubstituted maleimides also can be produced by this approach, potentially permitting the eventual synthesis of non-symmetrical bisindolylmaleimides.

A major problem with this general approach, however, is its limited applicability for synthesizing a variety of substituted bisindolylmaleimides. In particular, this approach can not be used with 1-substituted indole starting materials and thus is not easily adapted to the preparation of N-substituted indolylmaleimides.

The present invention is based on the discovery of a particularly simple approach to the synthesis of optionally substituted indolylmaleimides and especially the synthesis of symmetrical, as well as non-symmetrical, N-substituted bisindolylmaleimides using a palladium catalyst. Under preferred conditions, the desired compounds can be produced in acceptably high yields.

DESCRIPTION OF THE INVENTION

In a first aspect, the present invention is directed to a method of making an indolylmaleimide which comprises reacting an activated maleimide with an organometallic-3-indole in the presence of a palladium transition metal catalyst.

In another aspect, the present invention relates to an improved method for synthesizing an N-substituted indolylmaleimide and particularly compounds of the formula (I):

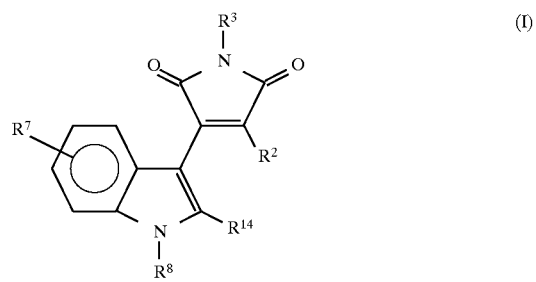

using an organometallic reagent and preferably an optionally N-substituted organometallic-3-indole as hereinafter described. The various substituents on the starting materials, and thus on the resulting indolylmaleimide product, can be selected from any of the wide variety of substitutents disclosed in the prior art, provided that the substituent does not interfere with the organometallic-based reaction of the invention. Preferably, $R^2$ is selected from a leaving group and an optionally substituted indol-3-yl, $R^3$ is selected from hydrogen and a protecting group, $R^7$'s are hydrogen or up to four optional substituents independently selected, for example, from halo, alkyl, hydroxy, alkoxy, haloalkyl, nitro, —NHCO(alkyl), or —NR$^9$R$^{10}$ where R$^9$ and R$^{10}$ are independently hydrogen, or methyl, $R^8$ is hydrogen or an optional substituent selected, for example, from an alkyl, haloalkyl, alkenyl, arylalkyl, alkoxyalkyl, hydroxyalkyl, monoalkylaminoalkyl, dialkylaminoalkyl, acylaminoalkyl, acyloxyalkyl, cyanoalkyl, amidinoalkyl, carboxyalkyl, alkoxycarbonylalkyl, aminocarbonylalkyl, aryl, alkylaryl, aminoalkyl, heteroaryl, carbonylalkyl, amidinothioalkyl, nitroguanidinoalkyl, a protecting group; an alkylglycose residue, a group of the formulae:

$$-(CH_2)_n-W-Het \quad -(CH_2)_n-T-\overset{\overset{V}{\|}}{C}-A$$

$$-(CH_2)_n-NH-\overset{\overset{NH}{\|}}{C}-Ar$$

[cyclopentyl-N(CH₃)₂ structure]

$$-(CH_2)_u-\underset{(CH_2)_q}{\overset{(CH_2)_p}{\diagup}}N-(CH_2)_s-R^{16}$$

[tetrahydrofuran structure]

$$-(CH_2)-O-\overset{\overset{O}{\|}}{C}-NH\text{-cycloalkyl}$$

$$-C_1-C_4\text{ alkyl-NH}-\overset{}{\underset{(CH_2)_a}{\diagdown}}$$

where:

Het signifies a heterocyclyl group,

W signifies NH, S or a bond,

T signifies NH or S,

V signifies O, S, NH, or NCN,

A signifies alkylthio, amino, monoalkylamino or dialkylamino, and

Ar signifies aryl;

$R^{16}$ is hydrogen, alkyl, haloalkyl, acetyl, aryl, —CH(aryl)$_2$, amino, monoalkylamino, dialkylamino, guanidino, —C(=N(alkoxy-carbonyl))—NH— (alkoxycarbonyl), amidino, hydroxy, carboxy, alkoxycarbonyl or heterocyclyl;

$R^{14}$ is hydrogen or an optionally substituted alkyl;

or $R^8$ and $R^{14}$ are linked together through a group of the formula:

$$[-(CH_2)_r-X-(CH_2)-]$$

where X is $$-\overset{\overset{(CH_2)_sR^{17}}{|}}{\underset{(CH_2)_sR^{18}}{C}}-$$

where $R^{17}$ and $R^{18}$ are independently hydroxy, carboxy, acyloxy, amino, monoalkylamino, dialkylamino, trialkylamino, azido, acylamino, alkoxycarbonyl, cyano, amidino or aminocarbonyl, and n is 1, 2, 3, 4, 5, or 6, p and q are independently 1, 2, 3, or 4, r is 1, 2, or 3, s is 0, 1, 2, or 3, t is 1 or 2, and u is 0 or 1.

In still another aspect, the present invention is more particularly directed to a method for preparing optionally N-monosubstituted and N,N-disubstituted bisindolylmaleimides, and particularly compounds of the formula:

[Structure of formula (II): bisindolylmaleimide with substituents R³ on maleimide N, R⁴ and R⁷ on benzene rings, R⁶ and R⁸ on indole nitrogens, R¹⁴ and R¹⁵ between indoles]

(II)

using an organometallic reagent and preferably an optionally N-substituted organometallic-3-indole as hereinafter described. As before, the various substituents on the starting materials and thus on the resulting bisindolylmaleimide product, can be selected from any of the wide variety of substituents disclosed in the prior art, provided that the substituent does not interfere with the organometallic-based reaction of the invention. Preferably, $R^3$ is selected from hydrogen and a protecting group, $R^4$'s and $R^7$'s are hydrogen or up to four optional substituents independently selected, for example, from halo, alkyl, hydroxy, alkoxy, haloalkyl, nitro, —NHCO(alkyl), or —NR$^9$R$^{10}$ where R$^9$ and R$^{10}$ are independently hydrogen or methyl, $R^6$ and $R^8$ are independently hydrogen or an optional substituent independently selected, for example, from an alkyl, haloalkyl, alkenyl, arylalkyl, alkoxyalkyl, hydroxyalkyl, monoalkylaminoalkyl, dialkylaminoalkyl, acylaminoalkyl, acyloxyalkyl, cyanoalkyl, amidinoalkyl, carboxyalkyl, alkoxycarbonylalkyl, aminocarbonylalkyl, aryl, alkylaryl, aminoalkyl, heteroaryl, carbonylalkyl, amidinothioalkyl, nitroguanidinoalkyl, a protecting group; an alkylglycose residue, a group of the formulae:

$$-(CH_2)_n-W-Het \quad -(CH_2)_n-T-\overset{\overset{V}{\|}}{C}-A$$

$$-(CH_2)_n-NH-\overset{\overset{NH}{\|}}{C}-Ar$$

[cyclopentyl-N(CH₃)₂ structure]

-continued $$-(CH_2)_u-\overset{(CH_2)_p}{\underset{(CH_2)_q}{\diagdown}}N-(CH_2)_s-R^{16}$$

[tetrahydrofuran ring structure]

$$-(CH_2)-O-\overset{O}{\underset{\|}{C}}-NH\text{-cycloalkyl}$$

$$-C_1-C_4\text{ alkyl-NH}-\overset{\triangle}{(CH_2)_a}$$

where:

Het signifies a heterocyclyl group,

W signifies NH, S or a bond,

T signifies NH or S

V signifies O, S, NH, or NCN

A signifies alkylthio, amino, monoalkylamino or dialkylamino, and

Ar signifies aryl;

$R^{16}$ is hydrogen, alkyl, haloalkyl, acetyl, aryl, —CH(aryl)$_2$, amino, monoalkylamino, dialkylamino, guanidino, —C(=N(alkoxy-carbonyl))—NH—(alkoxycarbonyl), amidino, hydroxy, carboxy, alkoxycarbonyl or heterocyclyl;

or $R^6$ and $R^8$ are joined together via an optionally substituted alkylene moiety, optionally having an internal ether (—O—), amino (—NH—) or amide (—CONH—) linkage;

$R^{14}$ and $R^{15}$ are independently hydrogen or an optionally substituted alkyl;

or $R^8$ and $R^{14}$ are linked together through a group of the formula;

$$[-(CH_2)_r-X-(CH_2)-]$$

where X is $$-\overset{(CH_2)_sR^{17}}{\underset{(CH_2)_sR^{18}}{C}}-$$

where $R^{17}$ and $R^{18}$ are independently hydroxy, carboxy, acyloxy, amino, monoalkylamino, dialkylamino, trialkylamino, azido, acylamino, alkoxycarbonyl, cyano, amidino or aminocarbonyl, and n is 1, 2, 3, 4, 5, or 6, p and q are independently 1, 2, 3, or 4, r is 1, 2 or 3, s is 0, 1, 2, 3, t is 1 or 2, and u is 0 or 1.

In a further aspect of the present invention, a method of producing a particular class of indolylmaleimide intermediates useful in connection with the present invention is provided which comprises reacting an optionally substituted, N-protected indole-3-acetamide in a polar, aprotic solvent, such as dimethyl formamide with an alkyl oxalate such as dimethyl oxalate and a strong organic base such as potassium tert-butoxide.

In accordance with one aspect of the present invention, indolylmaleimides and particularly compounds of formulae I and II can be prepared by reacting (1) an activated maleimide of the following formula (III):

[Formula (III): maleimide structure with R$^1$, R$^2$, R$^3$ substituents]

wherein $R^1$ is selected from a leaving group and an optionally substituted indol-3-yl, $R^2$ is a leaving group, and $R^3$ is —H or a protecting group, with (ii) an optionally substituted organometallic-3-indole reagent of the following formula (IV):

[Formula (IV): indole structure with R$^4$, R$^5$, R$^6$, R$^{14}$ substituents]

wherein $R^4$'s are hydrogen or up to four optional substituents independently selected, for example, from halo, alkyl, hydroxy, alkoxy, haloalkyl, nitro, —NHCO(alkyl), or —NR$^9$R$^{10}$ where R$^9$ and R$^{10}$ are independently hydrogen or methyl, $R^5$ is selected from —B(OH)$_2$, —ZnCl$_2$ and —Sn(R$^{12}$)$_3$, wherein R$^{13}$ is selected from an alkyl and an aryl, $R^6$ is selected from hydrogen or an optional substituent selected, for example, from an alkyl, haloalkyl, alkenyl, arylalkyl, alkoxyalkyl, hydroxyalkyl, monoalkylaminoalkyl, dialkylaminoalkyl, acylaminoalkyl, acyloxyalkyl, cyanoalkyl, amidinoalkyl, carboxyalkyl, alkoxycarbonylalkyl, aminocarbonylalkyl, aryl, alkylaryl, aminoalkyl, heteroaryl, carbonylalkyl, amidinothioalkyl, nitroguanidinoalkyl, a protecting group; an alkylglycose residue, a group of the formulae:

$$-(CH_2)_n-W-Het-(CH_2)_n-T-\overset{V}{\underset{\|}{C}}-A-(CH_2)_n-NH-\overset{NH}{\underset{\|}{C}}-Ar$$

[cyclopentyl-N(CH$_3$)$_2$ structure]

$$-(CH_2)_u-\overset{(CH_2)_p}{\underset{(CH_2)_q}{\diagdown}}N-(CH_2)_a-R^{16}$$

[tetrahydrofuran ring] $-(CH_2)-O-\overset{O}{\underset{\|}{C}}-NH\text{-cycloalkyl}$ $-C_1-C_4\text{alkyl-NH}-\overset{\triangle}{(CH_2)}.$ where:

Het signifies a heterocyclyl group,

W signifies NH, S or a bond,

T signifies NH or S,

V signifies O, S, NH, or NCN,

A signifies alkylthio, amino, monoalkylamino or dialkylamino, and

Ar signifies aryl;

$R^{16}$ is hydrogen, alkyl, haloalkyl, acetyl, aryl, —CH(aryl)$_2$, amino, monoalkylamino, dialkylamino, guanidino, —C(=N(alkoxy-carbonyl))—NH—

(alkoxycarbonyl), amidino, hydroxy, carboxy, alkoxycarbonyl or heterocyclyl;

$R^{14}$ is hydrogen or an optionally substituted alkyl;

or $R^6$ and $R^{14}$ are linked together through a group of the formula:

[—(CH$_2$)$_r$—X—(CH$_2$)—]

where X is

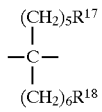

where $R^{17}$ and $R^{18}$ are independently hydroxy, carboxy, acyloxy, amino, monoalkylamino, dialkylamino, trialkylamino, azido, acylamino, alkoxycarbonyl, cyano, amidino or aminocarbonyl, and n is 1, 2, 3, 4, 5, or 6, p and q are independently 1, 2, 3, or 4, r is 1, 2, or 3, s is 0, 1, 2, or 3, t is 1 or 2, and u is 0 or 1.

The terms "halo" and "halogen" as used herein to identify substituent moieties, represent fluorine, chlorine, bromine or iodine, preferably chlorine or bromine.

The term "alkyl", alone or in combination, represents a cyclic, straight or branched chain saturated hydrocarbon group, which in the case of straight and branched chains, preferably has from one to four carbon atoms ($C_1$–$C_4$ alkyl) such as methyl, ethyl, n-propyl, isopropyl, cyclopropyl, n-butyl, isobutyl, sec-butyl, tert-butyl and the like and in the case of a cyclic hydrocarbon preferably has from three to seven carbon atoms, such as cyclopropyl and cyclohexyl. The term "substituted alkyl" is intended to include an alkyl group substituted with a substituent that does not prevent or interfere with the desired synthesis step.

The term "haloalkyl" is one such substituted alkyl, substituted with one or more halo atoms, and preferably is a $C_1$ to $C_4$ alkyl substituted with one to three halo atoms. One example of a haloalkyl is trifluoromethyl.

The term "alkoxy", used alone or in combination, is an alkyl, preferably a $C_1$ to $C_4$ alkyl, covalently bonded to the parent molecule through an —O— linkage alone or in combination. Examples of alkoxy groups are methoxy, ethoxy, propoxy, isopropoxy, butoxy and t-butoxy. An alkoxyalkyl is, for example, $CH_3$ $(CH_2)$—O—O $(CH_2)_m$— wherein m is from one to seven or preferably one to four. The term alkoxycarbonyl is, for example, t-butoxycarbonyl or BOC.

The term "aryl" when used alone or in combination represents a substituted or unsubstituted phenyl or naphthyl. Aryl may optionally be substituted with any substituent that does not prevent or interfere with the desired synthesis step and generally includes substitution with up to four and usually with one or two groups independently selected from hydroxy, carboxy, alkoxy, preferably a $C_1$ to $C_4$ alkoxy, an alkyl, preferably a $C_1$–$C_4$ alkyl, a haloalkyl, nitro, —NR$^9$R$^{10}$, —NHCO($C_1$–$C_4$ alkyl), —NHCO(benzyl), —NHCO(Phenyl), —SH, —S($C_1$–$C_4$ alkyl), —OCO($C_1$–$C_4$ alkyl), —SO$_2$(NR$^9$R$^{10}$), —SO$_2$($C_1$–$C_4$ alkyl), —SO$_2$ (phenyl), or halo wherein $R^9$ and $R^{10}$ are as defined above. The term aryloxy is one such aryl covalently bonded through an —O— linkage. The term arylalkyl can be considered a substituted alkyl and represents —(CH$_2$)aryl with m being an interger of generally 1 to 3, and preferably is benzyl. In contrast, the term alkylaryl can be considered a substituted aryl and may, for example, represent a moiety such as —aryl(CH$_2$)$_m$— CH$_3$ where m is an integer of generally 0 to 2.

The term "alkenyl" means a two to seven carbon, straight or branched hydrocarbon containing one or more double bonds, preferably one or two double bonds. Examples of alkenyl include ethenylene, propenylene, 1, 3, butadienyl, and 1, 3, 5-hexatrienyl.

The acyl moiety of an acylamino or acylaminoalkyl group is derived from an alkanoic acid containing a maximum of 7, preferably a maximum of 4, carbon atoms (e.g., acetyl, propionyl or butyryl) or from an aromatic carboxylic acid (e.g. benzoyl). An acyloxy is one such acyl bonded by an —O— linkage, for example, acetyloxy, $CH_3C(=O)O$—. An acylamino is, for example, $CH_3(C=O)NH$— (acetylamino). Likewise, an acylaminoalkyl is $CH_3$ $(C=O)NH(CH_2)_m$—.

The heterocyclic group denoted by "Het" or "heterocyclyl" can be a stable, saturated, partially unsaturated, or aromatic 5- or 6-membered heterocyclic group. The heterocyclic ring consists of carbon atoms and from one to three heteroatoms independently selected from the group consisting of nitrogen, oxygen, and sulfur. The heterocyclic group can be optionally substituted with one to three substituents independently selected from halogen, alkyl, hydroxy, alkoxy, haloalkyl, nitro, amino, acylamino, monoalkylamino, dialkylamino, alkylthio, alkylsulfinyl and alkylsulfonyl or, when the heterocyclyl group is an aromatic nitrogen-containing heterocyclic group, the nitrogen atom can carry an oxide group. Examples of such heterocyclyl groups are imidazolyl, imidazolinyl, thiazolinyl, pyridyl, indolyl, furyl, and pyrimidinyl.

The term "leaving group" (LG) as used in the specification and claims is readily understood by those skilled in the art. Generally, a leaving group is any group or atom that enhances the electrophilicity of the atom to which it is attached for easy displacement. Preferred leaving groups are triflate (—OSO$_2$CF$_3$), mesylate, tosylate, imidate, chloride, bromide, and iodide. Triflate is particularly preferred.

The term "alkylglycose residue" represents a glycose moiety linked in the C-1 position to the indolyl via a $C_2$ to $C_4$ alkyl. Glycoses included in alkylglycose residue are natural or unnatural 5 or 6 carbon sugars, preferably selected from allosyl, altrosyl, glucosyl, mannosyl, gulosyl, idosyl, galactosyl, talosyl, arabinosyl, xylosyl, lyxosyl, rhamnosly, ribosyl, deoxyfurananosyl, deoxypyranosyl, and deoxyribosyl. The glycose may be azide substituted, O-acetylated, O-methylated, amino, mono, and di-alkylamino substituted, or acylamino substituted. For example, alkylglycose residue includes:

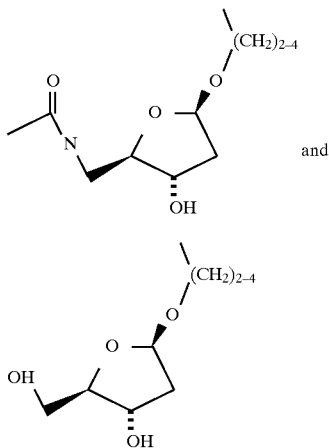

Under certain circumstances it is at least desired and often required to protect the nitrogen (N) of intermediates during the synthesis of the compounds of formulae (I) and (II) with suitable "protecting groups" which are known. Introduction and removal of such nitrogen protecting groups are well-known to those skilled in the art.

In this regard, the term "—NH protective groups" and "protecting group" when used in a similar context, and as used in the specification and claims, refers to sub-class of amino protecting groups that are commonly employed to block or protect the —NH functionality while reacting other functional groups on the compound. The species of protecting group employed in carrying out the method of the present invention is not critical so long as the derivatized —NH group is stable to the condition(s) of subsequent reaction(s) and can be removed at the appropriate point without disrupting the remainder of the molecule. T. W. Greene and P. Wuts, *Protective Groups in Organic Synthesis,* Chapter 7, pages 385–394 and 397–403, provide a list of commonly employed protecting groups for indoles and maleimides. Preferred indole protecting groups are trimethylsilylethoxymethyl, benzyl, tosyl, carbamate, amide, alkyl or aryl sulfonamide, while maleimide protecting groups include alkoxy, benzyl, dialkoxybenzyl, benzyloxyalkyl or allyl. The related term "protected —NH" defines a group substituted with an —NH protecting group as defined.

In certain circumstances there may also be a need to protect hydroxy groups and amino groups during the synthetic processes of the present invention. Those skilled in the art are familiar with such "hydroxy protecting groups" and such "amino protecting groups." The term "hydroxy protecting group" refers to one of the ether or ester derivatives of the hydroxy group commonly employed to block or protect the hydroxy group while reactions are carried out on other functional groups on a compound. The species of hydroxy protecting group employed is not critical so long as the derivatized hydroxy group is stable to the condition of subsequent reaction(s) and can be removed at the appropriate point without disrupting the remainder of the molecule. Preferred hydroxy protecting groups are tert-butyldiphenylsilyloxy (TBDPS), tert-butyldimethylsilyloxy (TBDMS), triphenylmethyl (trityl), mono- or di-methoxytrityl, or an alkyl or aryl ester.

The term "amino protecting group" refers to substituents of an amino group commonly employed to block or protect the amino functionality while reacting other functional groups on the compound. The species of amino-protecting group employed in carrying out the method of the present invention is not critical so long as the derivatized amino group is stable to the condition(s) of subsequent reaction(s) and can be removed at the appropriate point without disrupting the remainder of the molecule. Preferred amino-protecting groups are t-butoxycarbonyl, phthalimide, a cyclic alkyl, and benzyloxycarbonyl.

The term "activated maleimide" as used in the specification refers to a 3,4-disubstituted maleimide (pyrrolyl-2,5-dione), as represented by the root structure of formula (III) substituted with at least one leaving group that facilitates reaction with an organometallic reagent and especially with an optionally N-substituted organometallic-3-indole.

The term "indolylmaleimide" embraces a genus of compounds having as their root structure a 3-(indol-3-yl)-pyrrolyl-2,5-dione and includes the subgenus of "bisindolylmaleimides" having as their root structure a 3,4-(indol-3-yl)-pyrrolyl-2,5-dione, wherein the indol-3-yl moiety or moieties is/are optionally N-substituted, may optionally be substituted on the fused 6-membered aromatic ring of the indolyl moiety and may optionally be substituted at position 2 of the indol-3-yl moiety or moieties. Also included are those bisindolylmaleimides wherein the N-substituents of the indolyls are linked together through a bridging moiety as hereinafter described. The prior art describes a wide range of such optionally substituted indolylmaleimides and the present invention can advantageously be used to make such compounds as will be understood by those skilled in the art. Compounds falling within this definition of indolylmaleimide are described, inter alia, in U.S. Pat. No. 5,491,242 (PCT publication WO 95/35294), PCT publication WO 95/17182, and published European patent application EP 0657458, which are all incorporated herein by reference.

As used herein the term "organometallic-3-indole reagent" and similar phrases include compounds having as their root structure an indole substituted at the 3-position with a moiety selected from —B(OH)$_2$, —ZnCl$_2$ and —Sn (R$^{13}$)$_3$, wherein R$^{13}$ is selected from an alkyl and an aryl.

The reaction of the activated maleimide of formula (III) with an optionally substituted organometallic-3-indole of formula (IV), is conveniently carried out in an inert organic solvent, such as 1,2-dimethoxyethane (DME), dioxane, dichloromethane and acetonitrile or tetrahydrofuran (THF) generally at a temperature between about 0° C. and the reflux temperature of the reaction mixture, and preferably at a temperature within the range of 10° to 25° C.

The reaction is conducted in the presence of a palladium transition metal catalyst (Pd(0) and Pd(II) catalysts). The Pd(0) catalysts include Pd(Ph$_3$)$_4$, Pd$_2$(dibenzylidenacetone) (Pd$_2$dba$_3$), Pd/C, Pd(AsPh$_3$)$_4$, Pd(P(2-furyl)$_3$)$_4$, Pd(P(R$^{15}$)$_3$)$_4$ where R$^{15}$ is an alkyl or an aryl. The Pd(II) catalysts include Pd(OAc)$_2$, PdCl$_2$ (diphenylphosphinoferrocene) (PdCl$_2$(dppf)) and PdCl$_2$ (CH$_3$CN)$_2$.

The reaction generally is conducted in the presence of a base, such as sodium carbonate, and optionally a halogen ion source, such as lithium chloride. Preferably, the reaction is conducted in the presence of a fluoride ion, with cesium fluoride being the preferred source.

Following the initial reaction, any protecting groups can be replaced with a desired substituent using known procedures.

Many activated maleimide compounds falling within the scope of formula (III) are known compounds or are analogs of known compounds which can be prepared in a similar manner to the known compounds. Thus, procedures for preparing compounds of formula (III), especially those in which one or both of R$^1$ and R$^2$ are halo and particularly bromine, are well known. See Edge, S. et al., *Chemistry & Industry* (1991), p. 130. The organometallic reagents of formula (IV) also are known or can be prepared in a manner analogous to the known compounds. In this regard, please refer to Conway et al., *Heterocycles,* 30(1):627–633 (1990); Zheng et al., *Heterocycles,* 37(3):1761–1772 (1994); Zheng et al., *Tetrahedron Letters,* 34(14):2235–2238 (1993); Giusppe et al., *Tetrahedron Letters,* 35(15):2405–2408 (1994); Brenner et al., *Tetrahedron Letters,* 44:2887–2892 (1988); and Amat et al., *Tetrahedron Letters,* 35(5):793–796 (1994) which all are incorporated herein by reference.

Compounds of formula (I) and formula (II) are themselves useful as PKC inhibitors or represent intermediates useful for the preparation of compounds exhibiting PKC inhibitory activity. As noted above, PKC inhibitors are useful for treating a variety of conditions including cancer, central nervous system disorders, Alzheimer's, cardiovascular disease, dermatological diseases, inflammation, autoimmune diseases such as rheumatoid arthritis, and diabetic complications.

In one preferred aspect of the present invention, compounds of formula (I) or formula (II) are prepared by reacting (I) an optionally N-substituted indolylmalimide of the following formula (V), (which corresponds to an activated maleimide of formula (III) with $R^1$ being an optionally substituted indol-3-yl group):

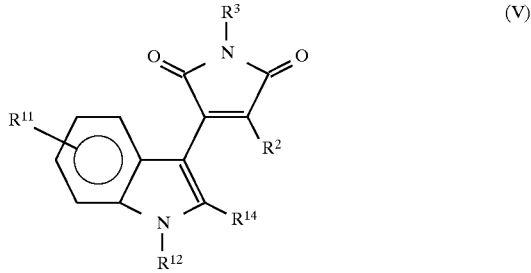

wherein the $R^{11}$ substituents are hydrogen or up to four are optionally and independently selected from halo, $C_1$ to $C_4$ alkyl, hydroxy, $C_1$ to $C_4$ alkoxy, halo, $C_1$ to $C_4$-alkyl, nitro, —NHCO($C_1$–$C_4$ alkyl) or —$NR^9R^{10}$ where $R^9$ and $R^{10}$ are independently hydrogen or, methyl, $R^{12}$ is an —NH protective group, $R^2$ is a leaving group, preferably a halo or triflate and most preferably a triflate, $R^{14}$ is hydrogen or an optionally substituted alkyl and $R^3$ is —H or an —NH protective group, with (ii) an organometallic reagent of formula (IV) wherein the $R^4$ substituents are hydrogen or up to four optional substituents independently selected, for example, from halo, alkyl, hydroxy, alkoxy, haloalkyl, nitro, —NHCO (alkyl), or —$NR^9R^{10}$ where $R^9$ and $R^{10}$ are independently hydrogen or methyl, $R^5$ is selected from —$B(OH)_2$, —$ZnCl_2$ and —$Sn(R^{13})_3$, wherein $R^{13}$ is selected from an optionally substituted alkyl and an optionally substituted aryl, and $R^6$ is an —NH protective group or hydrogen. The reaction is conducted under the conditions noted above.

In this preferred aspect, any protecting group is subsequently de-protected, using known techniques and procedures, to introduce, for example, a hydrogen, alkyl, aryl, substituted aryl, alkylaryl, aminoalkyl, heteroaryl, carbonylalkyl, amidinothioalkyl, nitroguanidinoalkyl or other desired moiety.

A particularly preferred feature of this aspect of the invention is the use of an indolylmaleimide of the following formula (VI) for preparing compounds of formula (I) or (II) by reaction with an organometallic reagent:

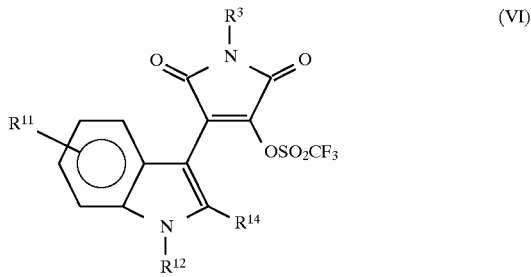

wherein $R^3$, $R^{11}$, $R^{14}$ and $R^{12}$ have the meanings identified above in connection with formula (V). Compounds of formula (VI) are useful for preparing compounds of formula (I) or (II) having PKC inhibitory activity or for preparing intermediates of PKC inhibitors.

In another preferred aspect of the present invention, an activated maleimide of formula (III) wherein both $R^1$ and $R^2$ are halo, and $R^3$ is —H or an —NH protective group, is reacted directly with an optionally N-substituted organometallic-3-indole reagent of formula (IV) wherein the $R^4$ substituents are hydrogen or up to four are optionally and independently selected, for example, from halo, alkyl, hydroxy, alkoxy, haloalkyl, nitro, —NHCO(alkyl), or —$NR^9R^{10}$ where $R^9$ and $R^{10}$ are independently hydrogen or methyl, $R^5$ is —$B(OH)_2$, and $R^6$ is an —NH protective group or hydrogen. If desired, the reaction can be conducted in two steps, introducing the maleimide substituents for the halogen atoms one at a time. In this way, non-symmetrical bisindolylmaleimides can be prepared. In this particular aspect, the protecting groups are subsequently de-protected, using known techniques and procedures, to introduce, for example, a hydrogen, alkyl, aryl, substituted-aryl, alkylaryl, aminoalkyl, heteroaryl, carbonylalkyl, amidinothioalkyl, nitroguanidinoalkyl or another desired moiety.

A compound of formula (III) wherein $R^1$ and $R^2$ both represent leaving groups, and especially halogen atoms are well known in the art. Preferred compounds of formula (III) wherein $R^1$ is an indol-3-yl and $R^2$ is a leaving group, i.e., compounds of formula (V), can be prepared using known techniques or can be produced using the method of this invention. In the latter case, a dihalomaleimide can be reacted with certain optionally substituted organometallic-3-indoles under conditions which lead to a monosubstituted product.

A first preferred embodiment of the present invention involves a process suitable for producing bisindolylmaleimides, including particularly non-symmetrical bisindolylmalemides starting from commercially available materials. In a particularly preferred approach, an optionally substituted N-protected indolyl-3-acetamide, such as an N-methylindole-3-acetamide can be made either by alkylation of an optionally substituted indole-3-acetamide with sodium hydride (NaH)/iodomethane ($CH_3I$) in dimethyl formamide (DMF) or by alkylation of an indole acetonitrile using iodomethane and an alkali metal hydroxide, such as potassium hydroxide, in acetone with subsequent conversion to the amide using hydrogen peroxide and sodium carbonate in dimethyl sulfoxide (DMSO) and procedures available in the prior art. The N-methylindole-3-acetamide thereafter can be cyclized in a novel process with an alkyl oxalate, such as dimethyl oxalate or diethyl oxalate followed by reaction with a strong organic base, such as potassium t-butoxide according to the following Scheme A to yield an optionally substituted 4-(indol-3-yl)-3-hydroxy pyrrole-2,5-dione. This reaction is conducted in a polar aprotic solvent, such as DMF.

Scheme A

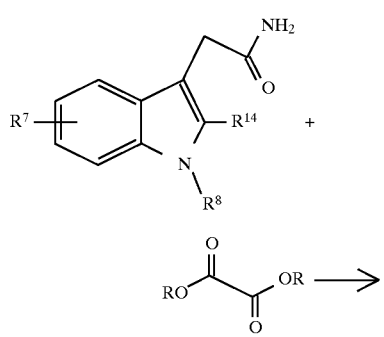

-continued
Scheme A

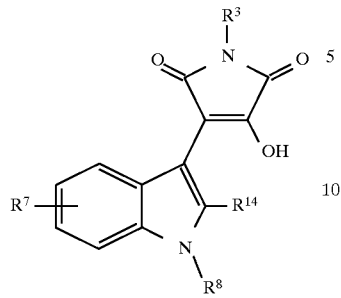

Following protection of the maleimide nitrogen with an —NH protective group, such as by treatment under alkylation conditions (sodium hydride/iodomethane in DMF), the hydroxy substituent on the maleimide is replaced with a leaving group such as (trifluoromethyl) sulfonyloxy (triflate) using known triflation conditions. A compound of formula (VI) can be prepared by reacting the optionally substituted 4-(indol-3-yl)-3-hydroxy pyrrole-2,5-dione with trifluoromethyl sulfonic anhydride in methylene chloride in the presence of a base (triethylamine). In an alternative approach, the hydroxy substituent on the maleimide can be replaced with a different leaving group such as bromide by reacting the optionally substituted 4-(indol-3-yl)-3-hydroxy pyrrole-2,5-dione with oxalyl bromide in the presence of DMF. The resulting compound then can be reacted with an organometallic reagent according to the present invention in the presence of a palladium transition metal catalyst, followed by deprotection of the protected nitrogens as desired to produce a compound of formula (I) or (II).

The reaction of the indolylmaleimide-triflate with an appropriately N-protected organometallic-3-indole is represented below as Scheme B and is conducted by adding, for example N-tosyl protected-3-indole boronic acid to the indolylmaleimide in dioxane preferably at a temperature of 0° to 20° C. with a temperature of about 15° C. being suitable. Higher temperatures can be used but Scheme B

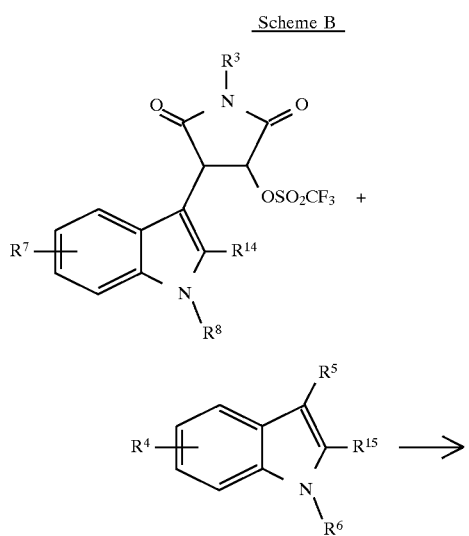

-continued
Scheme B

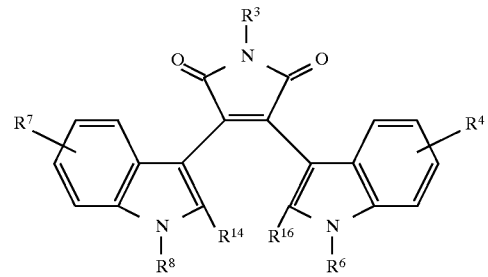

may provide a lower yield. Indeed, it was unexpectedly observed that the overall yield was strongly influenced by the initial temperature of the reaction mixture, with initiating the reaction at 15° C. being preferred. As noted, the reaction preferably is conducted in the presence of a palladium transition metal catalyst. A $Pd_2dba_3$— chloroform complex was found to be suitable. Higher yields are obtained when the reaction is conducted in the presence of fluoride ion such as provided by tetrabutylammonium fluoride, potassium fluoride and cesium fluoride, with cesium fluoride being the preferred source. The tosyl group subsequently can be deprotected in a known manner with potassium carbonate in a 3:1 volume mixture of methanol and water.

As noted above, by judicious selection of the various substituents on the starting active maleimide and the optionally N-substituted organometallic-3-indole reagent, the method of the present invention can be applied to prepare a wide variety of indolylmaleimides, and particularly bisindolylmaleimides.

One particularly useful class of indolylmaleimides, and particularly bisindolylmaleimides are those wherein the indolyl nitrogens of two indolyls are linked together through a bridging moiety. As noted above in connection with formula (II), the indolyl nitrogens can be joined together via an optionally substituted alkylene moiety, optionally having an internal ether (—O—), amino (—NH—) or an amide (—CONH—) linkage. Compounds of this class are represented by the following general formula (VII):

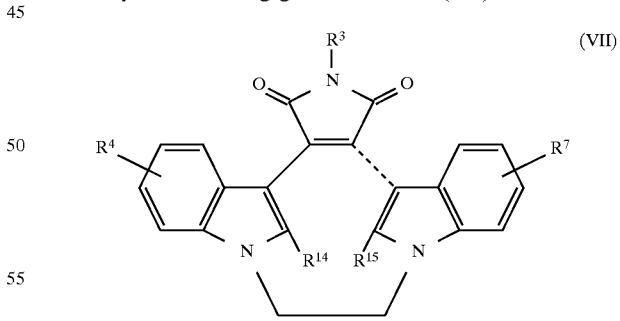

(VII)

where representative substituents for $R^3$, $R^4$, $R^7$, $R^{14}$ and $R^{15}$ are as previously defined. The dashed bond is intended to represent both the circumstance where there is a covalent bond and the circumstance where the maleimide and the indolyl instead independently have substituents at these positions. Compounds of this nature can be prepared by reacting an activated maleimide, such as described earlier in connection with formula (III) with an N-substituted organometallic-3-indole reagent of the following formula (VIII):

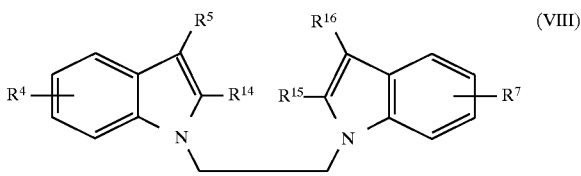

as shown below as Scheme C, wherein $R^4$, $R^5$, $R^7$, $R^{14}$ and $R^{15}$ are as previously defined, $R^{16}$ can be the same as $R^5$ or is a moiety that can be converted to $R^5$ for subsequent reaction with the maleimide, and wherein the bridging moiety is represented schematically by:

where the bridging moiety represents an optionally substituted alkylene moiety, optionally having an internal ether (—O—), amino (—NH—) or an amide (—CONH—) linkage.

Scheme C

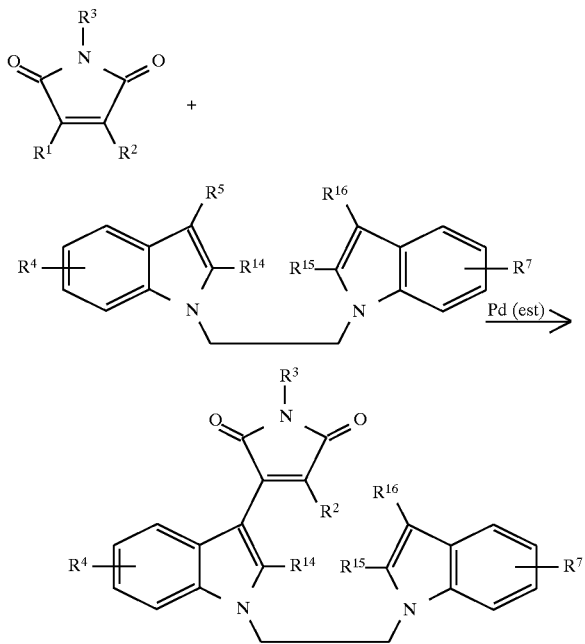

Particularly preferred are compounds where the bridging moiety is an alkylene of 4 to 14 carbon atoms. A wide variation is disclosed in the prior art for the optional substituents including alkyl, alkoxy, alkaryl, amino and the like, and the present invention is intended to embrace this variety.

Bisindole alkanes (optionally substituted and with optional hetero-atom internal linkages) of the above formula (VIII) can be prepared using procedures described in the published literature. For example, such compounds can be prepared by the slow addition of an optionally substituted dibromo alkane to a previously prepared reaction mixture containing an optionally substituted indole in a polar aprotic solvent such as dry dimethylformamide in the presence of an alkli metal salt, such as sodium hydride, or under other alkylation conditions, in a manner analogous to the procedure described in co-pending U.S. application Ser. No. 08/413,311, the disclosure of which is herein incorporated by reference. In an alternative approach, an optionally substituted dibromo alkane can be added to an approximately equal molar amount of an indole in the presence $Cs_2CO_3$ in a polar aprotic solvent, such as dimethylformamide, tetrahydofuran or acetonitrile, as described in published European application EP 0657458 the disclosure of which is incorporated herein by reference. This application also describes a process for producing a bridging moiety containing an internal ether (—O—), an amino (—NH—) or an amide (—CONH—) linkage, starting with a linking alkane molecule having a terminal protected carboxy, protected hydroxy, or protected amine and with a terminal leaving group.

Depending on the nature of the activated maleimide, compounds generally of formula (I) or (II)/(VII) are produced.

The products of the various reactions contemplated by the practice of the present invention can be isolated using conventional procedures including precipitation, extraction, distillation, chromatography, and the like.

As previously stated, the present process is useful in preparing compounds of formula (I) or (II). These compounds are PKC inhibitors and are useful in treating diseases implicated by PKC. The amount of a PKC inhibitory compound administered for therapeutic purpose is an amount that is capable of inhibiting PKC activity in mammals. The particular dose of the compound administered will, of course, be determined by the particular circumstances surrounding the case, including the compound administered, the route of administration, the particular condition being treated, and similar considerations. These compounds can be administered by a variety of routes including the oral, rectal, transdermal, subcutaneous, topical, intravenous, intramuscular or intranasal routes.

Experimental

The following preparations and examples are presented to illustrate and explain the invention. Unless otherwise indicated, all references to parts and percentages are based on weight and all temperatures are expressed in degrees Celsius. The scope of the invention is not construed as merely consisting of the following examples. In the following examples and preparations, melting point, nuclear magnetic resonance spectra, mass spectra, high pressure liquid chromatography over silica gel, N,N-dimethylformamide, palladium on charcoal, tetrahydrofuran, and ethyl acetate are abbreviated M.Pt., NMR, MS, HPLC, DMF, Pd/C, THF, and EtOAc respectively. The terms "NMR" and "MS" indicate that the spectrum was consistent with the desired structure.

PREPARATION 1: N-methylindole-3-acetamide

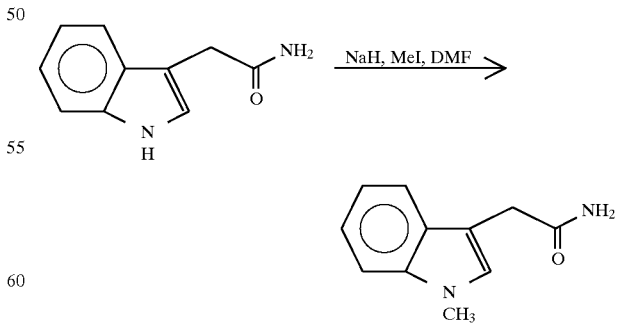

To an anhydrous DMF (125 mL) suspension of pentane-washed sodium hydride (2.73 g, 68.2 mmol, 1.2 eq) at 5° C. under nitrogen was added indole-3-acetamide (9.89 g, 56.8 mmol). After 15 minutes the ice bath was removed and stirring continued for 30 minutes. The reaction was cooled to 5° C. followed by dropwise addition of iodomethane (4.3 mL, 68.2 mmol, 1.2 eq) in DMF (15 mL). After the addition was complete the reaction was kept at 5° C. for 30 minutes and then allowed to warm to room temperature over 3 hours. TLC (9 CH$_2$Cl$_2$/1 CH$_3$CN×3) showed no staring material. The reaction was poured into water (200 mL) and EtOAc (600 mL) and the biphasic mixture separated. The aqueous portion was washed with EtOAc (5×200 mL). The combined EtOAc portions were washed with brine (2×250 mL), dried (MgSO$_4$), and evaporated in vacuo. In the process of evaporation a white solid came out of solution. It was filtered and dried to provide 6.78 g (63%) of a solid.

$^1$H NMR (d$_6$-DMSO): δ3.41 (2H, s); 3.69 (3H, s); 6.80 (1H, bs); 6.97 (1H, m); 7.09 (1H, m); 7.12 (1H, s); 7.29 (1H, bs); 7.34 (1H, d, J=8 Hz); 7.51 (1H, d, J=8 Hz)

MS: MW=188.23; observed (FD, MeOH) 188

IR: (KBr) 1625, 3438

EA: Anal. Calcd for C$_{11}$H$_{12}$N$_2$O: C, 70.19; H, 6.43; N, 14.88. Found: C, 70.39; H, 6.60; N, 14.91.

PREPARATION 2: 4-(1-methylindol-3-yl)-3-hydroxy-1H-pyrrole-2,5-dione

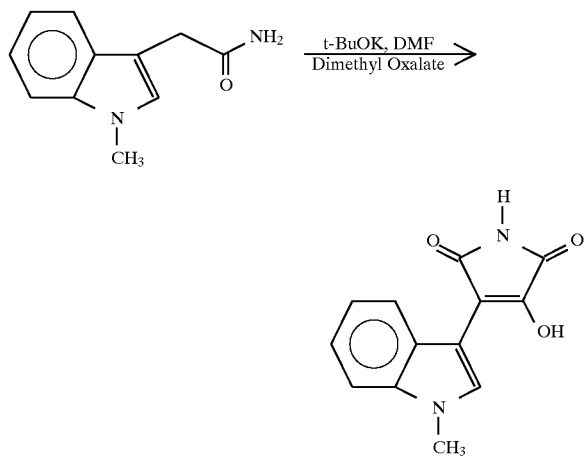

To an anhydrous DMF (100 mL) solution of N-methylindole-3-acetamide (6.06 g, 32.2 mmol) under nitrogen was added dimethyl oxalate (4.18 g, 35.4 mmol, 1.1 eq). The solution was cooled to 5° C. followed by addition of potassium t-butoxide (3.98 g, 35.4 mmol, 1.1 eq). The solution immediately turned a dark orange color. After 15 minutes another portion of potassium t-butoxide (3.98 g, 35.4 mmol, 1.1 eq) was added. After another 15 minutes the ice bath was removed and after 1 hour, TLC (EtOAc) showed no residual starting material. Over time, the reaction mixture developed into a thick precipitate. The reaction mixture was washed into a biphasic mixture of 1N HCl (250 mL)/EtOAc (500 mL) with the aid of water/EtOAc. The layers were separated and the aqueous phase was washed with EtOAc (3×200 mL). The combined EtOAc portions then were washed with brine (2×200 mL), dried (Na$_2$SO$_4$), filtered and evaporated in vacuo to provide 13.5 g of a dark yellow solid. The material was triturated in cold CH$_2$Cl$_2$ and filtered to give 6.73 g (86%) of an orange powder.

$^1$H NMR (d$_6$-DMSO): δ3.79 (3H, s); 7.04 (1H, m); 7.16 (1H, m); 7.40 (1H, d, J=8 Hz); 7.80 (1H, s); 8.09 (1H, d, J=8 Hz); 10.48 (1H, s); 11.71 (1H, bs)

$^{13}$C NMR(d$_6$-DMSO,500 MHz): δ32.56, 103.33, 106.18, 109.68, 119.25, 121.64, 122.29, 125.78, 130.23, 136.35, 147.09, 168.68, 172.42

MS: MW=242.23, observed (FD, MeOH) 242

IR: KBr; 1529, 1692, 1773, 3203

EA: Anal. Calcd for C$_{13}$H$_{10}$N$_2$O$_3$: C, 64.46; H, 4.16; N, 11.56. Found: C, 64.24; H, 4.18; N, 11.70.

PREPARATION 3: 4-(1-methylindol-3-yl)-3-hydroxy-1-methyl-pyrrole-2,5-dione

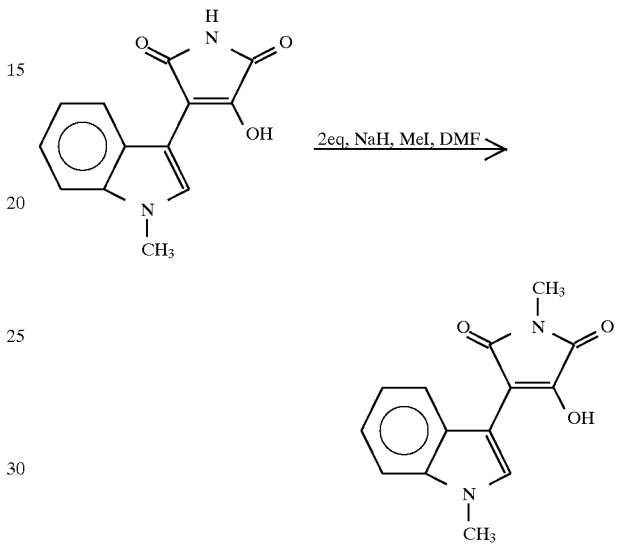

To an anhydrous DMF (150 mL) solution of 4-(1-methylindol-3-yl)-3-hydroxy-1H-pyrrole-2,5-ione (4.84 g, 20 mmol) under nitrogen at 5° C. was added NaH (1.76 g, 44 mmol, 2.2 eq). After 30 minutes, the ice bath was removed and stirring was continued for 1.5 hours. The reaction mixture was cooled to 5° C. and iodomethane (1.37 mL, 22 mmol, 1.1 eq) was added. Thereafter, the reaction mixture was allowed to warm slowly to room temperature and after 3 hours the reaction looked complete by TLC (2 EtOAc/1 hexane). A portion of the DMF was removed in vacuo and the remainder was poured into EtOAc (800 mL). The organic phase was washed with 1N HCl (200 mL) and backwashed with EtOAc (2×200 mL). The EtOAc portion then was washed with brine (2×200 mL), dried (Na$_2$SO$_4$), filtered and evaporated in vacuo to provide a red solid. The solid was recrystallized from CH$_2$Cl$_2$ to obtain 3.13 g of product. A second and third crop provided an additional 1.06 g of product for a total yield of 82%.

$^1$H NMR (d$_6$-DMSO): δ2.89 (3H, s); 3.80 (3H, s); 7.04 (1H, m); 7.16 (1H, m); 7.41 (1H, d, J=8 Hz); 7.80 (1H, s); 8.09 (1H, d, J=8 Hz); 11.90 (1H, bs)

MS: MW=256.26, observed (FD, MeOH) 256

IR: (CHCl$_3$) 1704, 2978, 3482

EA: Anal. Calcd for C$_{14}$H$_{12}$N$_2$O$_3$: C, 65.61; H, 4.72; N, 10.93. Found: C, 65.70; H, 4.76; N, 10.66.

PREPARATION 4: 4-(1-methylindol-3-yl)-3-triflate-1-methyl-pyrrole-2,5-dione (Triflate)

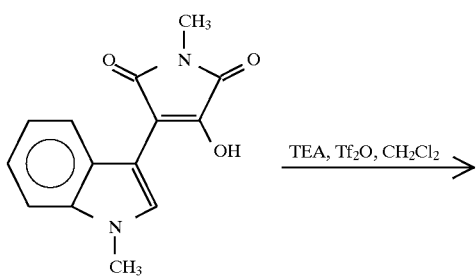

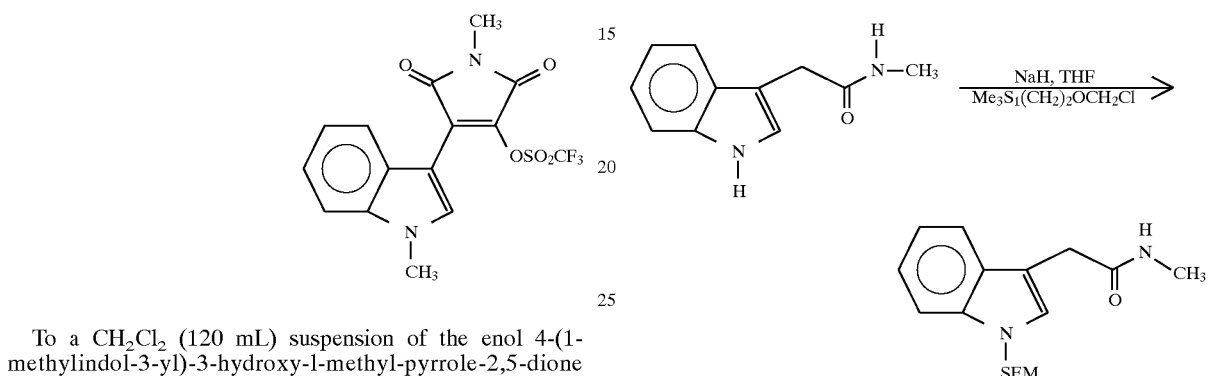

To a CH$_2$Cl$_2$ (120 mL) suspension of the enol 4-(1-methylindol-3-yl)-3-hydroxy-1-methyl-pyrrole-2,5-dione (1.54 g, 6 mmol) under nitrogen at −78° C. was added triethylamine (2.09 mL, 15 mmol, 2.5 eq) followed by slow addition of trifluoromethanesulfonic anhydride (1.51 mL, 9 mmol, 1.5 eq). The reaction mixture was stirred for 1 hour at −78° C. with the solid material gradually dissolving. The CH$_2$Cl$_2$ was removed in vacuo and the resulting residue was dissolved in EtOAc (200 mL). The EtOAc was washed with water (4×100 mL), 0.1N NaOH (100 mL), and then brine (2×100 mL), dried (MgSO$_4$), and was evaporated in vacuo to provide 2.35 g of an orange solid. Analytically pure material was obtained by tituration of this material in ether/hexane followed by filtration to provide 1.85 g (79%) of a yellow solid. (On a smaller scale analytically pure material has also been obtained without trituration in yields of 96%).

$^1$H NMR (d$_6$-DMSO): δ2.97 (3H, s); 3.91 (3H, s); 7.22–7.34 (2H, m); 7.58 (1H, d, J=8 Hz); 7.68 (1H, d, J=8 Hz); 8.25 (1H, s)

MS: MW=388.2, observed (FD, MeOH) found, 388

EA: Anal. Calcd for C$_{15}$H$_{11}$F$_3$N$_2$O$_5$S: C, 46.40; H, 2.86; N, 7.21. Found: C, 46.59; H, 3.12; N, 7.33.

PREPARATION 5: N-methyl-1H-indole-3-acetamide

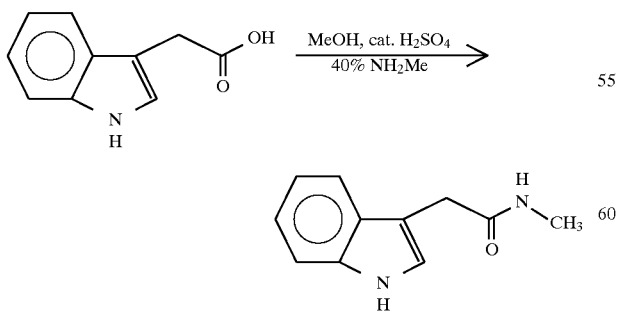

To a MeOH (200 mL) solution of indole-3-acetic acid (17.5 g, 100 mmol) was added concentrated sulfuric acid (2 mL) and the reaction mixture was refluxed for 5 hours. Following a workup and concentration in vacuo, the material was dissolved in MeOH (60 mL) and treated with 40% methylamine (30 mL) according to *Chem. Pharm. Bull.* (1990) 38, 2632. After workup, the material was passed through a silica pad with EtOAc to obtain 17.2 g (91%) of an oil. This oil was used without further purification in the subsequent reaction of Preparation 6.

PREPARATION 6: N-methyl-1-(2-(trimethylsilyl)ethoxy)-indole-3-acetamide

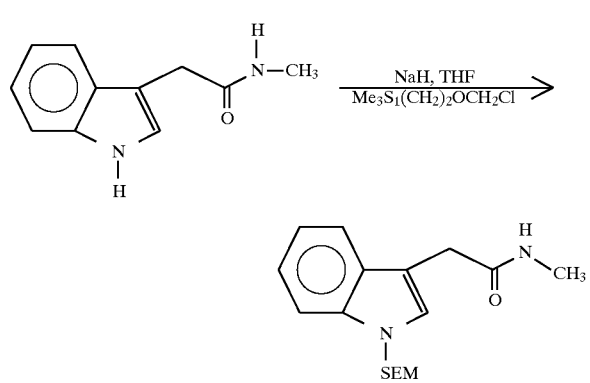

To an anhydrous THF (300 mL) solution of N-methyl-1H-indole-3-acetamide (17.2 g, 91.5 mmol) under nitrogen at 5° C. was added sodium hydride (4.4 g, 110 mmol, 1.2 eq). After 30 minutes the ice bath was removed and the reaction mixture was allowed to warm to room temperature over another 30 minutes. A THF (50 mL) solution of 2-(trimethylsilyl)ethoxy-methyl chloride (19.3g, 110 mmol, 1.2 eq) was then added dropwise over 30 minutes. After the addition was complete, the reaction mixture was stirred for 1 hour at which time TLC (4 vol. EtOAc/1 vol. hexane) showed no residual starting material present. The THF was removed in vacuo and the resulting residue partitioned between EtOAc (250 mL) and water (250 mL). The aqueous portion was separated and washed with EtOAc (2×100 mL). The combined EtOAc portions were washed with brine (2×200 mL), dried (Na$_2$O$_4$), filtered and evaporated in vacuo to provide 33.1 g of a yellow oil. The material was purified using a Waters 200OLC preparative HPLC to give 13.3 g of a white solid. The material was recrystallized from ether/hexane to provide 11.23 g (39%) of white flakes (mp. 92°–93° C.).

$^1$H NMR (d$_6$-DMSO): δ-0.10 (9H, s); 0.80 (2H, t, J=8 Hz); 2.55 (3H, d, J=4.5 Hz); 3.43 (2H, t, J=8 Hz); 3.46 (2H, s); 5.47 (2H, s); 7.03 (1H, m); 7.13 (1H, m); 7.27 (1H, s); 7.47 (1H, d, J=8 Hz); 7.54 (1H, d, J=8 Hz); 7.83 (NH, bm)

MS: MW=318.49, observed (FD, MeOH) 318

IR: (CHCl$_3$) 1531, 1660, 2957, 3432

EA: Anal. Calcd for C$_{17}$H$_{26}$N$_2$O$_2$Si: C, 64.11; H, 8.23; N, 8.80. Found: C, 63.85; H, 7.98; N, 9.04.

PREPARATON 7: N-(p-methoxybenzyl)-1-(methyl)-indole-3-acetamide

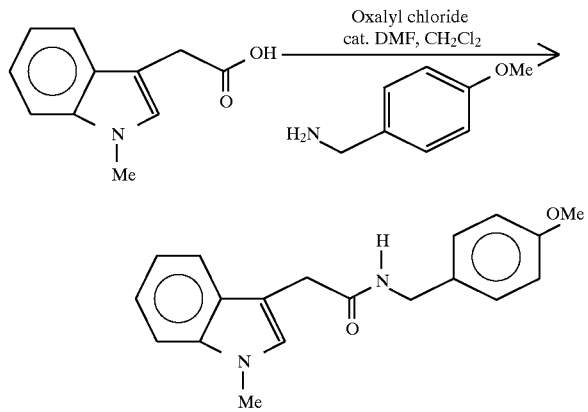

PREPARATION 8: N-(2,4-dimethoxybenzyl)-1-(methyl)-indole-3-acetamide

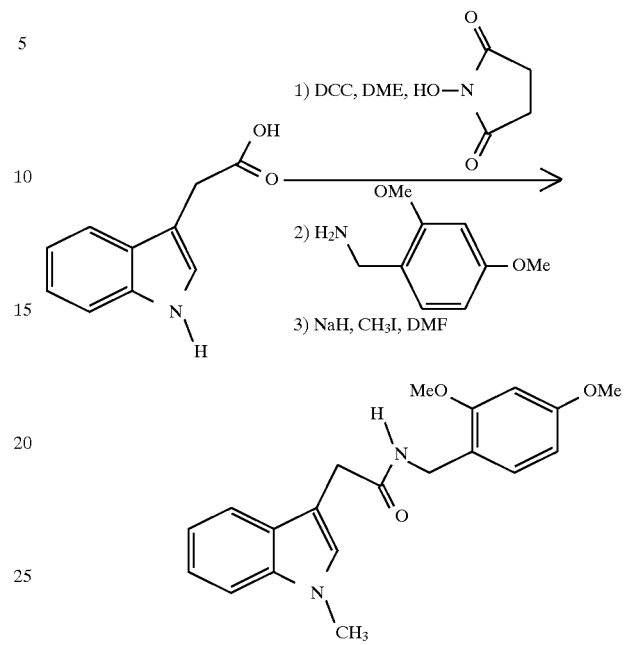

The starting N-methylindole-3-acetic acid was prepared by alkylation of ethyl 3-indole acetate with iodomethane (*Synthesis*, (1981) 461) followed by base hydrolysis.

To an anhydrous $CH_2Cl_2$ (30 mL) solution of N-methylindole-3-acetic acid (1.89 g, 10 mmole) cooled at 5° C. under nitrogen was added oxalyl chloride (2.2 mL, 25 mmole, 2.5 eq.) and 4 drops of DMF. The ice bath was removed after 1 hour and after 3 hours the reaction mixture was evaporated in vacuo overnight to remove all of the oxalyl chloride. The resulting brown oil was dissolved in anhydrous $CH_2Cl_2$ (40 mL) and cooled at 5° C. under nitrogen. A $CH_2Cl_2$ (20 mL) solution of 4-methoxybenzylamine (2.74 g, 20 mmole) was added dropwise and the reaction mixture was allowed to warm to room temperature over 18 hours. The $CH_2Cl_2$ was evaporated in vacuo and the resulting residue partitioned between EtOAc/water. The aqueous and organic layers were separated and the EtOAc washed again with water followed by back-extraction of the water with EtOAc. The combined EtOAc portions were washed with sodium bicarbonate, brine, dried ($Na_2SO_4$), filtered and evaporated in vacuo to provide 2.8 g of a brown oil. This material was passed through a flash column using 1 vol. hexane/1 vol. EtOAc to provide 2.10 g of a solid. Recrystallization of this material from ether/$CH_2Cl_2$ gave 1.73 g (49%) of white crystals.

$^1$H NMR ($d_6$DMSO): δ3.51 (2H, s); 3.69 (3H, s); 3.71 (3H, s); 4.16 (2H, d, J=6 Hz); 6.82 (2H, m); 7.00 (1H, m); 7.12 (4H, m); 7.35 (1H, d, J=8 Hz); 7.52 (1H, d, J=6 Hz); 8.31 (1H, t, J=6 Hz)

MS: MW=308.38; observed (FD, MeOH) 308

EA: Anal. Calcd for $C_{19}H_{20}N_2O_2$: C, 74.03; H, 6.54; N, 9.08. Found: C, 74.06; H, 6.53; N, 9.21.

To a dimethoxyethane (100 mL) solution of 3-indole acetic acid (8.76 g, 50 mmol) and N-hydroxysuccinimide (5.75 g, 50 mmol) under nitrogen at 5° C. was added dicyclohexyl carbodiimide (10.32 g, 50 mmol). The reaction mixture was stirred for 20 minutes and then allowed to stand in a refrigerator for 16 hours. The reaction mixture then was filtered and the filtrate was evaporated in vacuo to provide a gummy residue. Recrystaized of this material from isopropanol provided 7.33 g (54%) of a white solid.

MS: MW=272.26; observed (FD, MeOH) 272

To a $CH_2Cl_2$ (130 mL) solution of the succinimide ester from above (7.00 g, 25.7 mmol) under nitrogen was added a $CH_2Cl_2$ (20 mL) solution of 2,4-dimethoxy-benzylamine (5.15 g, 30.8 mmol, 1.2 eq). The reaction mixture was stirred at room temperature for 16 hours. The $CH_2Cl_2$ was removed in vacuo and the resulting residue was dissolved in EtOAc. The EtOAc was washed with water (2×), 1N NaOH (1×), 1N HCl (1×), and brine (2×), dried ($Na_2SO_4$), filtered and evaporated in vacuo to provide 8.33 g (quantitative yield) of a solid.

An anhydrous DMF (200 mL) solution of the indole acetamide (8.33 g, 25.7 mmol) was treated in a manner similar to the above Preparation 1 with iodomethane (1.70 mL, 27 mmol). Subsequent workup and recrystallization from $CH_2Cl_2$/hexane provided 6.65 g (77%) of a white solid.

$^1$H NMR (CDCl$_3$): δ3.38 (3H, s); 3.72 (2H, s); 3.76 (3H, s); 3.77 (3H, s); 4.28 (2H, d, J=6 Hz); 6.23 (NH, bt); 6.28 (1H, d, J=2 Hz); 6.36 (1H, dd, J=2 Hz, J=8 Hz); 6.96 (1H, s); 7.10 (2H, m); 7.24 (1H, m); 7.32 (1H, d, J=8 Hz); 7.47 (1H, d, J=8 Hz)

MS: MW=338.41, observed (FD, MeOH) 338

EA: Anal. Calcd for $C_{20}H_{22}N_2O_3 \cdot 0.2M$ $CH_2Cl_2$: C, 68.27; H, 6.35; N, 7.88. Found: C, 68.51; H, 6.45; N, 8.08.

PREPARATIONS 9–11: 4-(1-substituted indolyl-3-yl)-3-hydroxy-1-substituted-pyrrole-2,5-diones

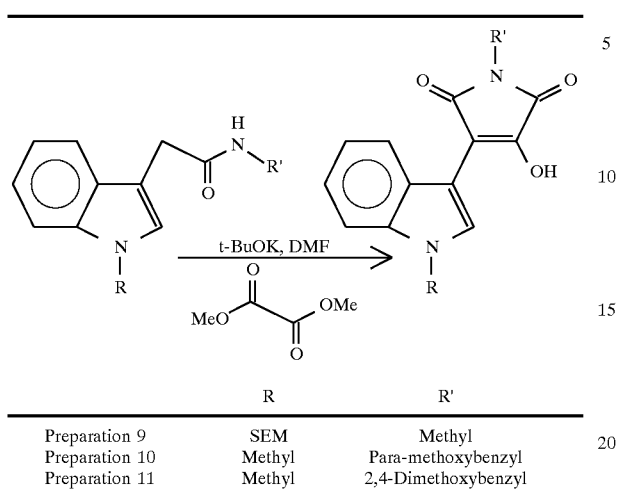

| | R | R' |
|---|---|---|
| Preparation 9 | SEM | Methyl |
| Preparation 10 | Methyl | Para-methoxybenzyl |
| Preparation 11 | Methyl | 2,4-Dimethoxybenzyl |

Using the procedure reported in Preparation 2, and as starting materials the products of Preparations 6, 7, and 8, respectively, the corresponding parent compounds (confirmed by NMR, MS, EA) were produced in 62%, 37% and 71% yield respectively.

Using the procedure of Preparation 4, the compounds of Preparations 9, 10 and 11 can be converted to the corresponding triflates.

PREPARATION 12: Dichloro-N-methylmaleimide

A 3L-three-necked flask fitted with a magnetic stir bar, digital thermocouple/thermometer, nitrogen purge and solid addition funnel was charged with 450 g (269.5 mol) of dichloromaleic anhydride, 191 g (282.8 mol) of methylamine hydrochloride and 1.6 L of acetic acid. The reaction mixture was then cooled to 10° C., and 160 g NaOMe added from the solid addition funnel over 1 hour while keeping the temperature between 10°–12° C. The reaction mixture was allowed to stir at room temperature for 42 hours (24 hours is sufficient) then heated to 100° C. for 3 hours. HPLC analysis at this time indicated that all the starting material had disappeared. The reaction was cooled to room temperature and 2L water was added. The mixture was then cooled to 3°–10° C. for 1 hour and filtered at 4° C. The solids were then rinsed with 2L of cold deionized water. The pale yellow solid dried in an air oven overnight to afford 360 g (75%) yield of the titled compound.

PREPARATION 13: 4-(1-methylindol-3-yl)-3-bromo-1-(4-methoxybenzyl)-pyrrole-2,5-dione

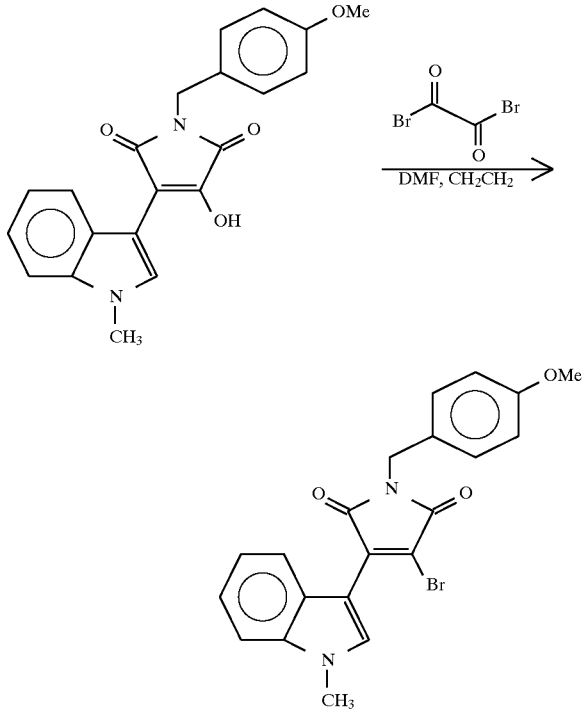

To a $CH_2Cl_2$ (0.5 mL) suspension of the enol 4-(1-methylindol-3-yl)-3-hydroxy-1-(4-methoxybenzyl)-pyrrole-2,5-dione (26 mg, 0.072 mmol) under nitrogen was added DMF (10 uL, 0.094 mmol, 1.3 eq). The suspension was cooled to 5° C. and treated with oxalyl bromide (8 uL, 0.086 mmol, 1.2 eq). The suspension was stirred 1 hr at room temperature at which time TLC (1 hexane/1 EtOAc) showed no reaction. The reaction was treated with more DMF (10 uL, 0.094 mmol) and oxalyl bromide (8 uL, 0.086 mmol) and refluxed for 16 hr. The $CH_2Cl_2$ was removed in vacuo and the resulting residue partitioned between EtOAc and saturated $NaHCO_3$ solution. The layers were separated and the aqueous washed with more EtOAc. The combined EtOAc portions were washed with brine, dried ($Na_2SO4$), and evaporated in vacuo to provide 29 mg of a red gum. The material was purified on a flash column by elution with 4 hexane/1 EtOAc to provide 12 mg (39%) of product.

$^1$H NMR ($d_6$DMSO): δ3.70 (3H, s); 3.88 (3H, s); 4.63 (2H, s); 6.87 (1H, d, J=8 Hz); 7.16–7.30 (2H, m); 7.54 (1H, d, J=8 Hz); 7.89 (1H, d, J=8 Hz); 8.10 (1H, s)

MS: MW=425.28, observed (FD, MeOH) found, 425, 427 (Br isotopes)

EXAMPLE 1: 4-(1-methyl-3-indolyl)-3-(1-tosyl-3-indolyl)-1-(methyl)-pyrrole-2,5-dione.

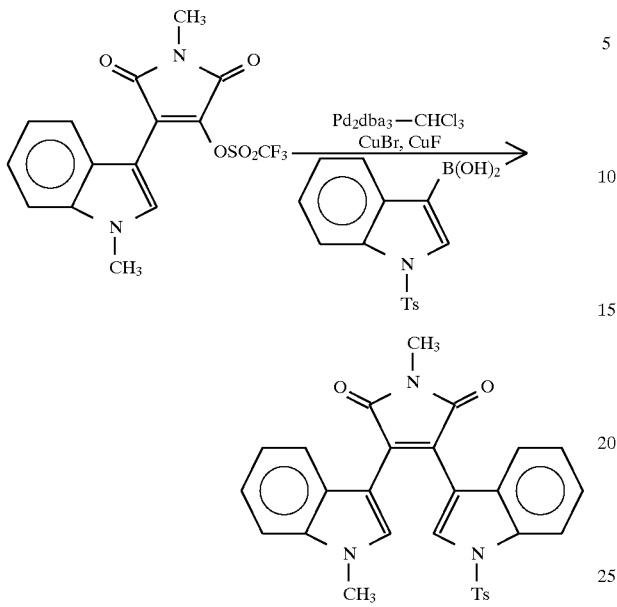

An anhydrous dioxane (15 mL) solution of triflate (777 mg, 2.0 mmole) under nitrogen was placed in a water bath at 15° C. Tris(dibenzylideneacetone) dipalladium-chloroform complex (80 mg, 4 mol percent), N-tosyl-3-indolylboronic acid (693 mg, 2.2 mmol, 1.1 eq), cesium fluoride (1.00 g, 6.6 mmol, 3 eq to boronic acid) and cesium bromide (1.40 g, 6.6 mmol) were added and after 10 min. the water bath was removed and the reaction mixture was allowed to warm to ambient temperature. After 5 hours, TLC (3 ppv hexane/1 ppv EtOAc) showed approximately 10–20% triflate remaining and so the reaction was allowed to continue for 18 hrs. Thereafter, the dioxane was removed in vacuo and the resulting residue partitioned between EtOAc (75 mL) and water (50 mL). The layers were separated and the aqueous portion was washed with EtOAc (2×50 mL). The combined EtOAc portion was washed with 0.1N NaOH (2×50 mL) (NaOH backwashed with EtOAc), and brine (2×50 mL), dried (MgSO$_4$), filtered and evaporated in vacuo to provide 1.21 g of a crude brown solid. The material was purified by flash chromatography by sequential elution with 9 ppv hexane/1 ppv EtOAc, 5/1, 3/1, 2/1 and 1 ppv hexane/1 ppv EtOAc to provide 559 mg (55%) of a yellow solid.

$^1$H NMR (d$_6$-DMSO): δ2.34 (3H, s); 3.02 (3H, s); 3.84 (3H, s); 6.08 (1H, m); 6.28 (1H, d, J=8 Hz); 6.84 (2H, m); 6.92 (1H, t, J=8 Hz); 7.15 (1H, m); 7.37 (3H, m); 7.85 (3H, m); 7.96 (1H, s); 8.02 (1H, s)

MS: MW=509.58, observed (FD, MeOH) 509

IR: (CHCl$_3$) 1543, 1700

EA: Anal. Calcd for C$_{29}$H$_{23}$N$_3$O$_4$S: C, 68.35; H, 4.55; N, 8.25. Found: C, 68.51; H, 4.60; N, 8.17

EXAMPLE 2: 4-(1-methyl-3-indolyl)-3-(1H-3-indolyl)-1-(methyl)-pyrrole-2,5-dione

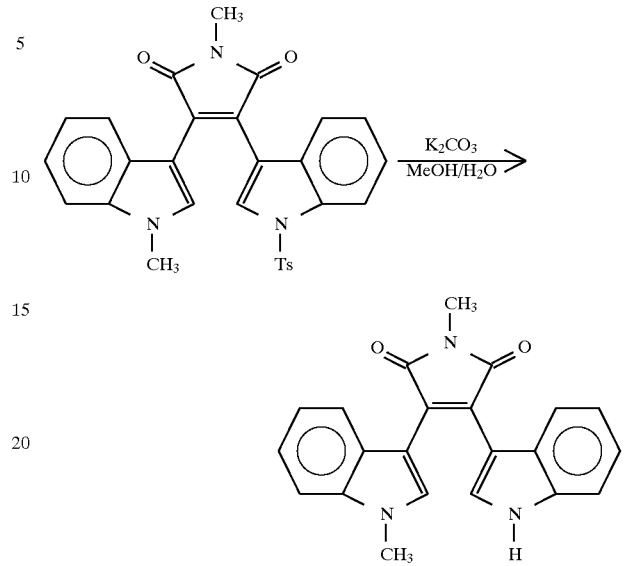

Deprotection of the indolyl in Example 1 by removal of the tosyl substitutent proceeded as follows. To a MeOH/water (3 mL/1 mL) suspension of the 4-(1-methyl-3-indolyl)-3-(1-tosyl-3-indolyl)-1-(methyl)-pyrrole-2,5-dione (102 mg, 0.2 mmole) was added potassium carbonate (138 mg, 1.0 mmole, 5 eq) and the reaction mixture was refluxed for 8 hours and then heated at 60° C. for 16 hours. The reaction mixture turned into a red solution after 1–2 hours. The MeOH was removed in vacuo and the resulting residue partitioned between EtOAc/1N HCl (10 mL/10 mL). The aqueous phase was separated and washed with more EtOAc (10 mL). The combined EtOAc portions were washed with brine (2×20 mL), dried (MgSO$_4$), filtered and evaporated in vacuo to provide 74 mg of a red gum. The material was applied to a flash column and eluted with 98 ppv CH$_2$Cl$_2$/1 ppv isopropanol/1 ppv acetonitrile to provide 67 mg (84%) of a red solid which contained 0.5 mole of CH$_2$Cl$_2$.

$^1$H NMR (d$_6$-DMSO): δ3.01 (3H, s); 3.82 (3H, s); 6.60 (2H, m); 6.69 (1H, d, J=8 Hz); 6.80 (1H, d, J=8 Hz); 6.97 (2H, m); 7.34 (1H, d, J=8 Hz); 7.38 (1H, d, J=8 Hz); 7.70 (1H, d, J=3 Hz); 7.79 (1H, s); 11.64 (NH, m)

MS: MW=355.40, observed (FD, MeOH) 356

EA: Anal. Calcd for C$_{22}$H$_{17}$N$_3$O$_2$.0.5M CH$_2$Cl$_2$; C, 67.93; H, 4.56; N, 10.56. Found: C, 68.46; H, 4.65; N, 10.54.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention. Those skilled in the art will recognize variations in the processes as described above and will recognize appropriate modifications of the reaction conditions based on the above disclosure for maling the compounds of formulae (I) and (II). Also, alternative starting materials which can be used to prepare the formulae (I) and (II) compounds using the methods of the present invention are known or can be prepared by known methods.

We claim:

1. An indolylmaleimide of the formula:

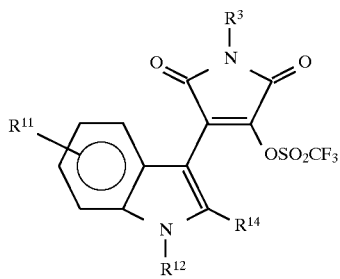

wherein $R^3$ is —H or a protecting group, $R^{11}$'s are hydrogen or up to four substituents independently selected from halo, $C_1$ to $C_4$ alkyl, hydroxy, $C_1$ to $C_4$ alkoxy, halo, $C_1$ to $C_4$-alkyl, nitro, —NHCO($C_1$–$C_4$ alkyl) and —NR$^9$R$^{10}$ where $R^9$ and $R^{10}$ are independently hydrogen or methyl, $R^{12}$ is an —NH protective group and $R^{14}$ is hydrogen or an optionally substituted alkyl.

2. The indolylmaleimide of claim 1 wherein $R^{12}$ is selected from the group consisting of trimethylsilylethoxymethyl, benzyl, and tosyl, or wherein $R^{12}$ together with the indole N forms a carbamate, an amide, an alkyl sulfonamide or an aryl sulfonamide.

3. The indolylmaleimide of claim 1 wherein $R^{11}$ is hydrogen.

4. The indolylmaleimide of claim 1 wherein $R^{14}$ is hydrogen.

5. The indolylmaleimide of claim 1 wherein $R^{12}$ is methyl.

6. The indolylmaleimide of claim 1 wherein $R^{11}$ and $R^{14}$ are hydrogen and $R^{12}$ is methyl.

7. The indolylmaleimide of the formula:

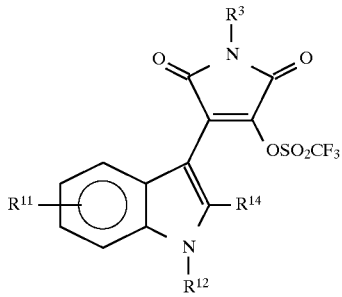

wherein $R^3$ is —H or methyl, $R^{11}$'s are hydrogen or up to four substituents independently selected from halo, $C_1$ to $C_4$ alkyl, hydroxy, $C_1$ to $C_4$ alkoxy, halo, C, to $C_4$-alkyl, nitro, —NHCO($C_1$–$C_4$ alkyl) and —NR$^9$R$^{10}$ where $R^9$ and $R^{10}$ are independently, hydrogen or methyl, $R^{12}$ is selected from the group consisting of trimethylsilylethoxymethyl benzyl, and tosyl, or wherein $R^{12}$ together with the indole N forms a carbamate, an amide, an alkyl sulfonamide or an aryl sulfonamide and $R^{14}$ is hydrogen or an optionally substituted alkyl.

8. The indolylmaleimide of claim 7 wherein $R^{11}$ is hydrogen.

9. The indolylmaleimide of claim 7 wherein $R^{11}$ is hydrogen.

10. The indolylmaleimide of claim 7 wherein $R^{12}$ is methyl.

11. The indolylmaleimide of claim 7 wherein $R^{11}$ and $R^{14}$ are hydrogen and $R^{12}$ is methyl.

* * * * *